US010898687B2

(12) United States Patent
Souza et al.

(10) Patent No.: US 10,898,687 B2
(45) Date of Patent: Jan. 26, 2021

(54) FOLDABLE IV CATHETER SECUREMENT DRESSING FOR PROTECTING AGAINST INADVERTENT CONTAMINATION

(71) Applicant: Becton, Dickinson and Company, Franklin Lakes, NJ (US)

(72) Inventors: Marcel A. Souza, Provo, UT (US); Bart D. Peterson, Farmington, UT (US); Darin L. Peterson, Taylorsville, UT (US); Azhar J. Khan, Salt Lake City, UT (US); Kelly D. Christensen, Centerville, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 489 days.

(21) Appl. No.: 15/803,098

(22) Filed: Nov. 3, 2017

(65) Prior Publication Data
US 2018/0050175 A1    Feb. 22, 2018

Related U.S. Application Data

(63) Continuation of application No. 13/706,105, filed on Dec. 5, 2012, now Pat. No. 9,827,396.
(Continued)

(51) Int. Cl.
*A61M 25/02* (2006.01)
*A61F 13/02* (2006.01)

(52) U.S. Cl.
CPC ......... *A61M 25/02* (2013.01); *A61F 13/0246* (2013.01); *A61F 13/0259* (2013.01);
(Continued)

(58) Field of Classification Search
CPC .............. A61F 13/0246; A61F 13/0259; A61F 13/0269; A61M 2025/0246; A61M 2025/0253
See application file for complete search history.

(56) References Cited

U.S. PATENT DOCUMENTS

| 4,669,458 A | 6/1987 | Abraham et al. |
| 4,909,243 A | 3/1990 | Frank et al. |

(Continued)

FOREIGN PATENT DOCUMENTS

| GB | 2464662 | 4/2010 |
| JP | 2002-527173 | 8/2002 |

(Continued)

*Primary Examiner* — Deanna K Hall
(74) *Attorney, Agent, or Firm* — Kirton & McConkie; Craig Metcalf; Kevin Stinger

(57) ABSTRACT

Sterile intravenous catheter securements and securement dressings that provide simpler, more effective, and lower risk intravenous catheter placement and securement in a patient are described. Catheter securement dressings may include one or more adhesive portions positioned and configured to maintain a position of a catheter assembly following catheterization. Catheter securement dressings may be secured to a patient with an adhesive portion, and the catheter assembly may then be placed into the patient through an access opening in the catheter securement dressing. Portions of catheter securement dressings may then by folded over and adhered to each other and portions of the catheter assembly to secure the catheter assembly to the patient.

10 Claims, 6 Drawing Sheets

Related U.S. Application Data

(60) Provisional application No. 61/568,079, filed on Dec. 7, 2011, provisional application No. 61/568,087, filed on Dec. 7, 2011.

(52) U.S. Cl.
CPC ............... *A61M 2025/0246* (2013.01); *A61M 2025/0273* (2013.01)

(56) References Cited

U.S. PATENT DOCUMENTS

| | | | |
|---|---|---|---|
| 5,086,763 A | 2/1992 | Hathman | |
| 5,282,791 A | 2/1994 | Lipton et al. | |
| 9,968,760 B2 * | 5/2018 | Chawki | A61M 25/02 |
| 2012/0271240 A1 | 10/2012 | Andino et al. | |

FOREIGN PATENT DOCUMENTS

| | | |
|---|---|---|
| JP | 2003-526482 | 9/2003 |
| JP | 2011-525824 | 9/2011 |
| WO | 95/04511 | 2/1995 |
| WO | 2011/060197 | 5/2011 |

* cited by examiner

FOLDABLE IV CATHETER SECUREMENT DRESSING FOR PROTECTING AGAINST INADVERTENT CONTAMINATION

RELATED APPLICATIONS

This application is a continuation of U.S. application Ser. No. 13/706,105 filed on Dec. 5, 2012, entitled FOLDABLE IV CATHETER SECUREMENT DRESSING FOR PROTECTING AGAINST INADVERTENT CONTAMINATION, which claims the benefit of U.S. Provisional Patent Application No. 61/568,079 filed on Dec. 7, 2011, entitled NEXIVA INTEGRATED SECUREMENT PLATFORM, and U.S. Provisional Patent Application No. 61/568,087 filed on Dec. 7, 2011, entitled FOLDABLE IV CATHETER DRESSING PROTECTING AGAINST INADVERTANT CONTAMINATION, the disclosures of which are incorporated herein by reference in their entireties.

BACKGROUND OF THE INVENTION

This disclosure relates generally intravenous catheters. More specifically, this disclosure discusses various methods of using and systems of sterile intravenous catheter securement dressings to permit sterile securement of the intravenous catheter to a patient.

Generally, vascular access devices are used for communicating fluid with the vascular system of patients. For example, catheters are used for infusing fluid (e.g., saline solution, medicaments, and/or total parenteral nutrition) into a patient, withdrawing fluids (e.g., blood) from a patient, and/or monitoring various parameters of the patient's vascular system.

Intravenous (IV) catheter assemblies are among the various types of vascular access devices. Over-the-needle peripheral IV catheters are a common IV catheter configuration. As its name implies, an over-the-needle catheter is mounted over an introducer needle having a sharp distal tip. The introducer needle is generally a venipuncture needle coupled to a needle assembly that helps guide the needle and facilitates its cooperation with the catheter. At least the inner surface of the distal portion of the catheter tightly engages the outer surface of the needle to prevent peelback of the catheter and, thereby, to facilitate insertion of the catheter into the blood vessel. The catheter and the introducer needle are often assembled so that the sharp distal tip of the introducer needle extends beyond the distal tip of the catheter. Moreover, the catheter and needle are often assembled so that during insertion, the bevel of the needle faces up, away from the patient's skin. The catheter and introducer needle are generally inserted at a shallow angle through the patient's skin into a blood vessel.

Following catheterization, the intravenous catheter assembly is secured to the patient to prevent premature and/or unintended removal of the catheter assembly. A dressing is often applied to limit exposure to the catheter site and further protect the catheter assembly from contaminants and from being inadvertently moved or dislodged. In some instances, the clinician holds the inserted catheter assembly in place by digital pressure while preparing and applying a dressing and adhesive strips to the catheter assembly. This process generally requires both hands of the clinician, and therefore the clinician commonly prepares the dressing and adhesive strips prior to inserting the catheter assembly into the patient, requiring placing the dressing and adhesive strips in a temporary location while attempting to secure the catheter assembly. This temporary location placement may provide additional opportunities for infective agents to contact the catheter assembly and catheter insertion site from the dressing and adhesive strips. In other instances, a first clinician catheterizes the patient while a second clinician prepares and applies the dressing and adhesive strips to secure the inserted catheter assembly, lessening the infection risk, but greatly increasing the resources and effort required to place a catheter. Thus, the process of securing the inserted catheter assembly to the patient can be time consuming, cumbersome, and in some instances, add undue risk of infection.

BRIEF SUMMARY OF THE INVENTION

This disclosure relates generally to sterile intravenous catheter securements and securement dressings that provide simpler, more effective, and lower risk intravenous catheter placement and securement in a patient. More specifically, this disclosure discusses various methods and systems for using sterile securements and securement dressings with an intravenous catheter to permit sterile, easy, and efficient securement of the intravenous catheter to a patient.

Some exemplary catheter securement dressings may include a body comprising an upper portion and a lower portion, the lower portion comprising an access opening, a first adhesive layer configured to adhere the catheter securement dressing to skin, and a second adhesive layer configured to adhere the upper portion to the lower portion. The dressing may also include a release liner covering at least one of the first and second adhesive layers. The release liner may include a release tab and a pull tab extending from the body, the pull tab being free from both the first and second adhesive layers.

In some embodiments, the first adhesive layer may be on a surface of the lower portion, and the second adhesive layer may be on a surface of the upper portion. The dressing may also include a fold line. At least one of the first and second adhesive layers may include an anti-microbial agent. In other embodiments, the dressing may be configured to be folded in half such that only the bottom surface is exposed when in the folded configuration. In such embodiments, the first adhesive layer is configured to adhere the catheter securement dressing to the skin of a patient, and the second adhesive layer may be configured to secure the dressing layer in the folded configuration Exemplary methods of applying exemplary catheter securement dressings may include attaching the catheter securement to the skin of a patient at a desired catheter site, placing a catheter device in the desired catheter site, and folding the catheter securement to secure the catheter device in the desired catheter site. Exemplary methods may also include removing a release liner prior to folding the catheter securement dressing, the release liner covering an adhesive layer prior to removal of the release liner. In some methods, at least a portion of the catheter device may be secured between two layers of the catheter securement dressing after the folding. Similarly, the placing of the catheter device may be done through the access opening in the securement dressing.

BRIEF DESCRIPTION OF THE DRAWINGS

In order that the manner in which the above-recited and other features and advantages of disclosed embodiments are obtained and will be readily understood, a more particular description of the systems and methods briefly described above will be rendered by reference to specific embodiments thereof, which are illustrated in the appended drawings. Understanding that these drawings depict only typical embodiments and are not, therefore, to be considered to be limiting of its scope. Exemplary embodiments of the disclosed systems and methods will be described and explained with additional specificity and detail below through the use of the accompanying drawings in which.

Figure 1:
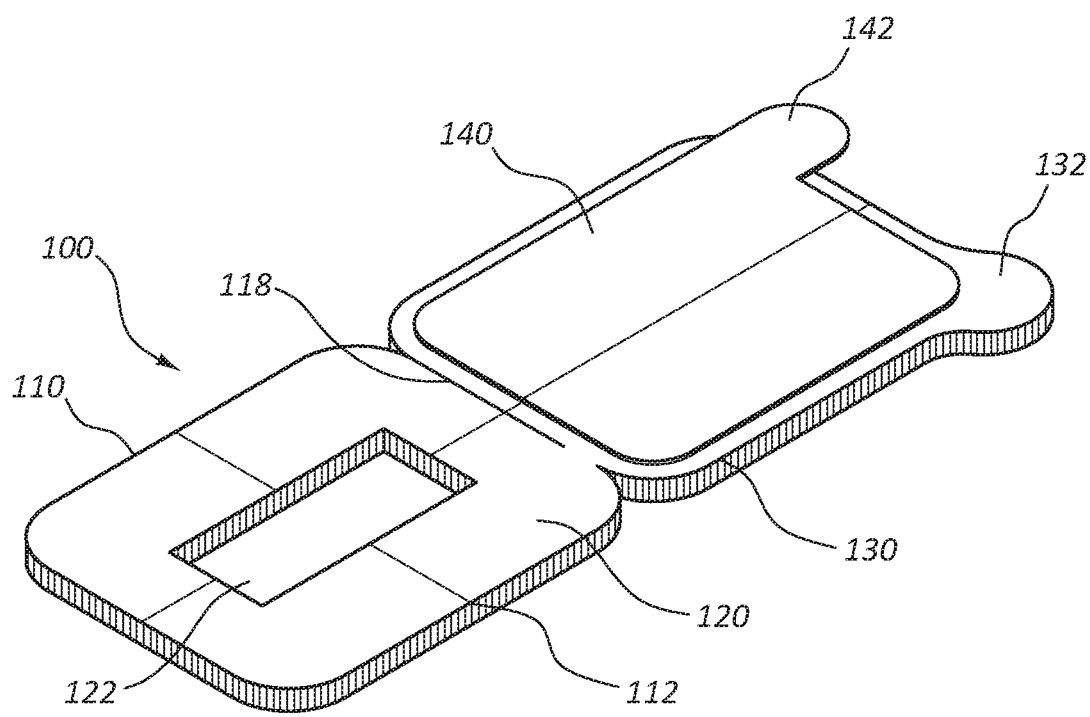
FIG. 1 illustrates a perspective view of an exemplary catheter securement dressing.

The Figures illustrate specific aspects of exemplary catheter securement dressing and methods for making and using such devices as described below. Together with the following description, the Figures demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices. Moreover, the Figures may show simplified or partial views, and the dimensions of elements in the Figures may be exaggerated or otherwise not in proportion for clarity and instruction.

DETAILED DESCRIPTION OF THE INVENTION

The following description supplies specific details in order to provide a thorough understanding. Nevertheless, the skilled artisan would understand that the described catheter securement dressings and methods of making and using them can be implemented and used without employing these specific details. Indeed, the catheter securement dressing and associated methods can be placed into practice by modifying the illustrated devices and methods and can be used in conjunction with any other apparatus and techniques conventionally used in the industry.

Generally, this disclosure is related to systems and methods for securing a catheter assembly to a patient following catheterization. In some instances, a catheter securement may include one or more adhesive portions which are positioned and configured to maintain a position of a catheter assembly following catheterization. Some embodiments of catheter securements and securement dressings may be secured to a patient with an adhesive portion, and the catheter assembly may then be placed into the patient. In some embodiments, the catheter assembly may be placed through an access opening in a catheter securement dressing. A release liner covering and protecting another of the adhesive portions may be removed to reveal an adhesive portion upon placement of the catheter assembly. The adhesive portions may include an anti-microbial agent to aid in reducing the risk of infection at the catheter insertion site. Portions of the catheter securement or securement dressing may then by folded over onto itself and adhered to itself and portions of the catheter assembly to secure the catheter assembly to the patient. The catheter securement and securement dressing may be configured such that a clinician applying a catheter assembly to a patient may be able to easily secure the catheter assembly and, in some embodiments, provide a sterile dressing without the need for additional materials.

Figure 2:
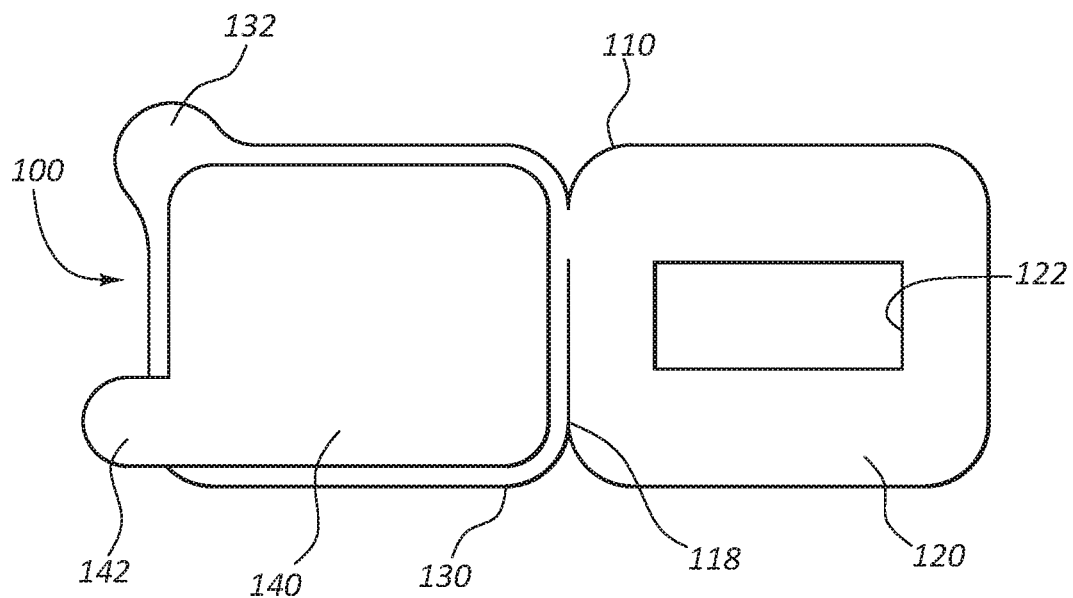
FIG. 2 illustrates a top view of the catheter securement dressing of FIG. 1
Figure 3:
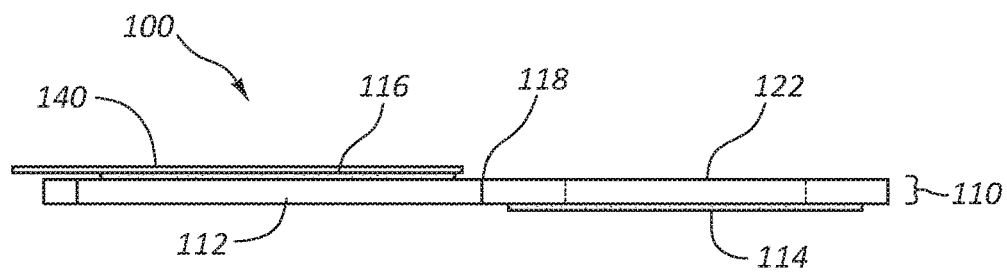
FIG. 3 illustrates a side view of the catheter securement dressing of FIG. 1.

Referring now to FIGS. 1-3, a catheter securement dressing 100 is shown. Catheter securement dressing 100 may include a dressing body 110, with an upper portion 120 and a lower portion 130 foldable about fold line 118, as will be further described in more detail below. Lower portion 120 may include adhesive layer 114 on a contact side of lower portion 120 for contact and adhesion with the skin of a patient. Upper portion 130 may include adhesive layer 116 on the opposite side of body 110 from adhesive layer 114 to provide adhesion between a top face of lower portion 120 and the adhesive layer 116 of upper portion 130 when catheter securement dressing 120 is folded about fold line 118 and in place. Release liner 140 may be provided to protect adhesive layer 116 from inadvertent and premature contact until the catheter site is ready for catheter securement dressing 100 to be folded into its final position, as is described in further detail below.

Lower portion 120 may also include access opening 122 to provide a window for placement of a catheter. Access opening 122 may be a window, enclosed on each lateral side, or it may be a slit or strip opening in lower portion 120 to provide access to the catheter placement site. Similarly, access opening 122 may be any suitable or desirable shape, such as a rectangle as shown in the Figures, or a square, triangle, or other polygonal shape, or it may be an oval, cartioid, lenticular, or other curved shape suitable for access of a catheter to an intravenous catheter site when lower portion 120 is affixed to a patient.

Upper portion 130 may include close tab 132 to provide a gripping area to fold upper portion 130 about fold line 118 to contact with lower portion 120. Close tab 132 may be formed so as to make folding catheter securement dressing 100 intuitive for clinicians using the device. Release liner 140 may also be included on upper portion 130 to protect adhesive layer 116 from inadvertent and premature contact. Release liner 140 may further include release tab 142 to aid in removing release liner 140 when a clinician is ready to fold catheter securement dressing 100 into place. In some embodiments, a second release liner may be provided to protect adhesive layer 114 on lower portion 120 prior to use. As such, release liners may be placed over any adhesive portion to preserve the adhesive properties and sterility prior to securement to the patient. In some embodiments, adhesive layer 116 and release liner 140 may cover the top surface of lower portion 120 in place of or in addition to upper portion 130.

Adhesive layers 114, 116 may include any type or form of adhesive that is suitable for use with the methods and embodiments discussed. For example, adhesive layers 114, 116 may be a spray-on adhesive, adhesive film, or any other type of adhesive application. Further, in some embodiments adhesive layers 114, 116 may be formed of or include a polymer-based pressure sensitive adhesive. For example, when a polymer-based pressure sensitive adhesive is used in adhesive layer 114, a bond may formed between adhesive layer 114 and the patient's skin by applying light pressure between lower portion 120 and the skin. Adhesive layer 114 may further include a slight liquid carrier that facilitates bonding with the skin. In some instances, adhesive layer 114 may include a single-use glue, such that the adhesive loses its adhesive properties once removed from the skin. In some embodiments, adhesive layers 114, 116 may also include an anti-microbial agent to aid in maintaining a sterile intravenous insertion site.

In other instances, adhesive layers 114, 116 may be formed of or include a multiple-use glue, wherein the adhesives may allow the dressing to be applied repeatedly. For example, a multiple-use glue for adhesive layer 116 or adhesive layer 114 may be desired to permit subsequent inspection, or adjustment of the catheter position following securement, or both. This may be desirable for situations where the tip of the catheter becomes occluded within the vein, thereby requiring the catheter to be moved slightly to reestablish patency. This may also be a desirable feature where the placement of the catheter or the catheter securement dressing 100 becomes uncomfortable to the patient.

In some embodiments, adhesive layer 116 may include a contact adhesive that adheres only when placed into contact with a compatible adhesive, which may cover all or part of the top surface of lower portion 120 such that when upper portion 130 is folded over onto lower portion 120, the adhesives contact and bond. In such embodiments, release liner 140 may not be required. In some embodiments, adhesive 114, 116 may be formed any shape, pattern, size and/or configuration necessary to provide a desired securement between the catheter adapter and the skin of the patient, and between the lower portion 120 and the upper portion 130.

Release liner 140 may include any material or combination of materials that permit temporary bonding between release liner 140 and adhesive layer 116, wherein upon removal of release liner 140 from adhesive layer 116, the adhesive is left undisturbed. Non-limiting examples of compatible materials for release liner 140 may include plastic film, paper, plastic, metal foil, plastic coated paper, wax coated paper, wax coated plastic, plastic coated foil, and wax coated foil. Similarly, release liner 140 may be coated, impregnated, or layered with a release agent, an anti-microbial agent, or both. In some embodiments, only on the portion of release liner in contact with adhesive layer 116 may have the release properties or agents, and in other embodiments, release liner 140 may have the same manufacture throughout.

As best shown in FIG. 3, body 110 may be formed with a dressing layer 112 extending throughout upper portion 120 and lower portion 130. Dressing layer 112 may be formed of any suitable dressing or wound management material for use in dressing catheter insertion sites. For example, dressing layer 112 may be formed using transparent polyurethane dressings, gauze dressings, moisture reactive dressings, or any other suitable material for intravenous site dressings. Body 110 may also include anti-microbial agents or have an anti-microbial film. Body 110 may be any suitable thickness for use as an intravenous catheter dressing and securement. Fold line 118 may be established by the edge of adhesive layer 114, or may be encouraged as a thinner, scored, or otherwise weakened line in body 110 or dressing layer 112.

Figure 4:
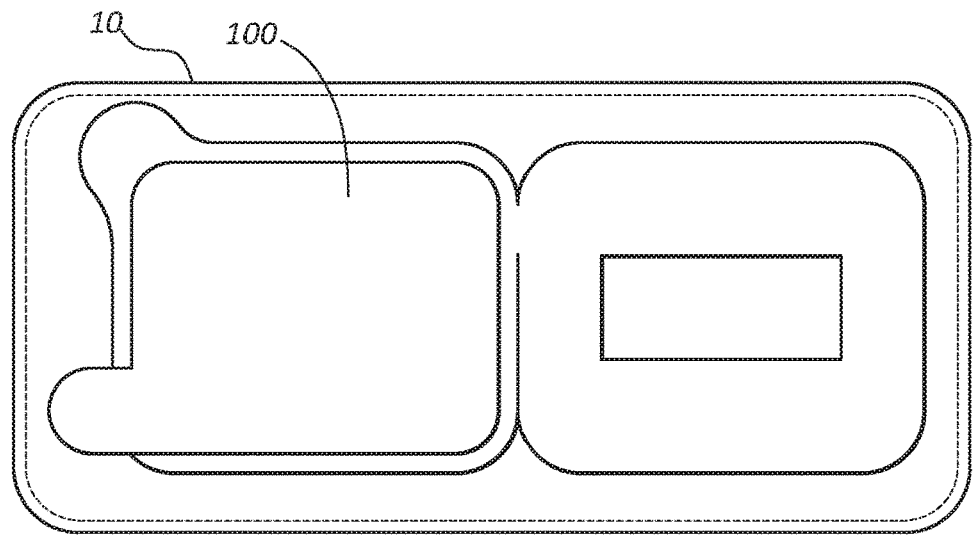
FIG. 4 illustrates a top view of an exemplary packaged catheter securement dressing.

Turning now to FIG. 4, catheter securement dressing 100 may be provide in a sterile, sealed package 10. In some embodiments, sealed package 10 may act as a release liner for adhesive layer 114, such that when catheter securement dressing 100 is removed from sealed package 10, adhesive layer 114 is exposed and ready to be placed on the skin of a patient. In other embodiments, as described above, adhesive layer 114 may be covered with a release liner requiring removal after removal from sealed package 10 and prior to application to the skin of a patient. Sealed package 10 may be any packaging suitable for use with sterile medical supplies, such as the many different varieties currently used as such.

Figure 5:
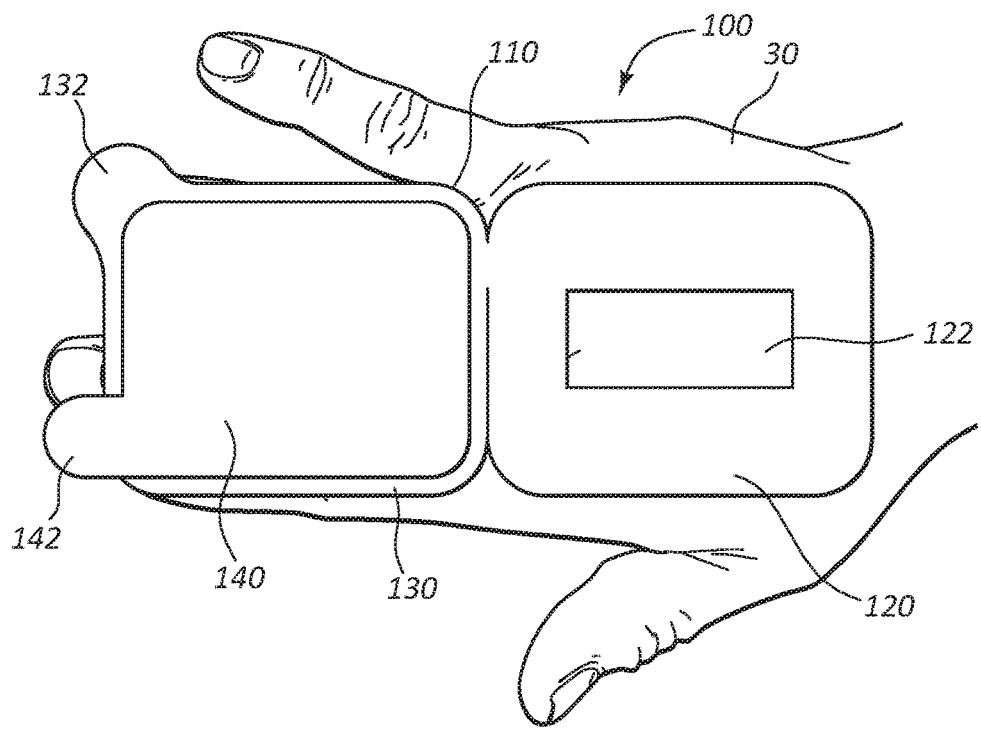
FIGS. 5-9 illustrate a top view of the catheter securement dressing of FIG. 1 placed on the hand of a patient in successive stages of application of an intravenous catheter and the catheter securement dressing.

Turning now to FIGS. 5-9, catheter securement dressing 100 may be applied to the skin on a patient 30 in preparation for insertion of catheter device 20. In some embodiments, applying catheter securement dressing 100 may include cleaning and preparing the catheter site by a clinician. Once the site on patient 30 is prepared, catheter securement dressing 100 may be removed from sealed package 10. As shown in FIG. 5, once removed from sealed package 10, catheter securement dressing 100 may be positioned over the catheter site on patient 30 such that access opening 122 may be centered over the catheter site. Lower portion 120 may then be pressed onto skin of patient 30 so that adhesive layer 114 attaches lower portion 120 to the skin of patient 30. In embodiments where a separate release liner is included with adhesive layer 114, the release liner may be removed prior to placement of access window over the desired catheter site.

Figure 6:
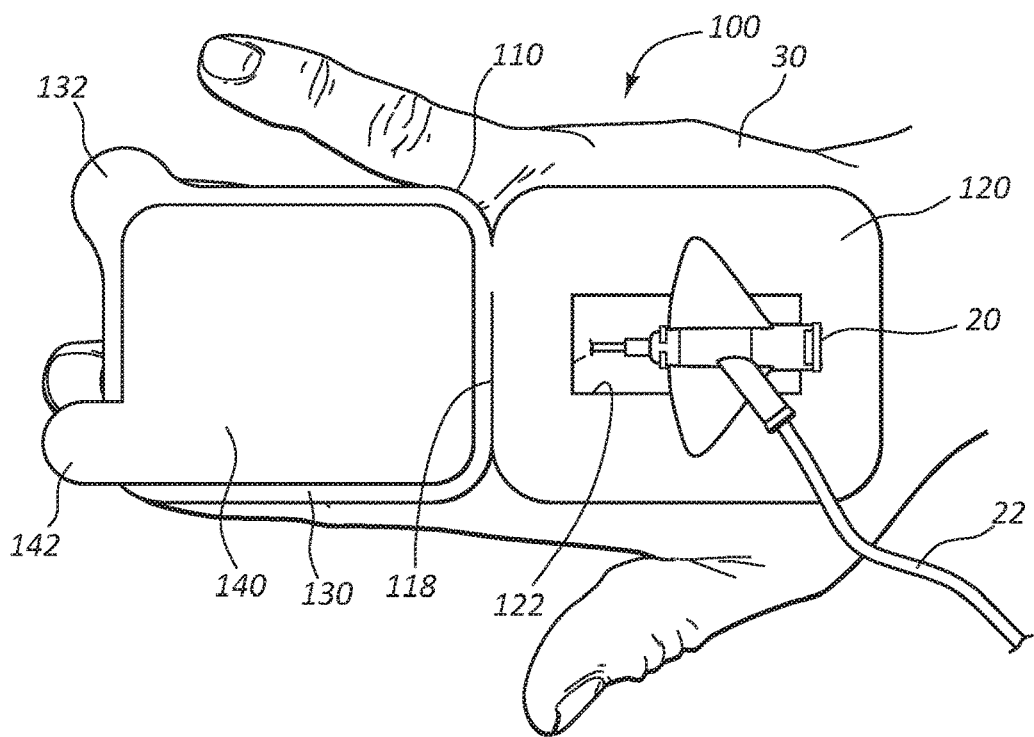
Figure 7:
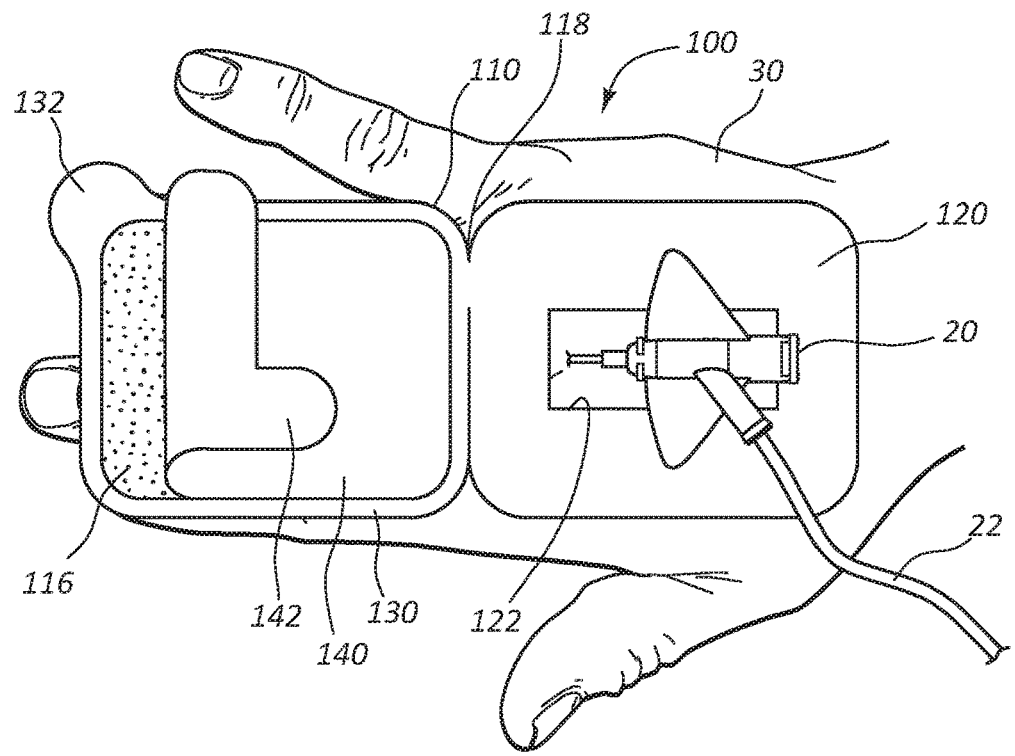

As shown in FIG. 6, once catheter securement dressing 100 is in position, a clinician may insert catheter device 20 into patient 30 through access opening 122 of lower portion 120. Tube 22 may be extended away from the outer edges of lower portion 120 to provide fluid access to catheter device 20 once catheter securement dressing 100 is in final placement and covering catheter device 20. As shown in FIG. 7, once catheter device 20 is placed, release liner 140 may be removed to expose adhesive layer 116. Release liner 140 may be removed by pulling on release tab 142. Release liner 140 may be disposed of.

Figure 8:
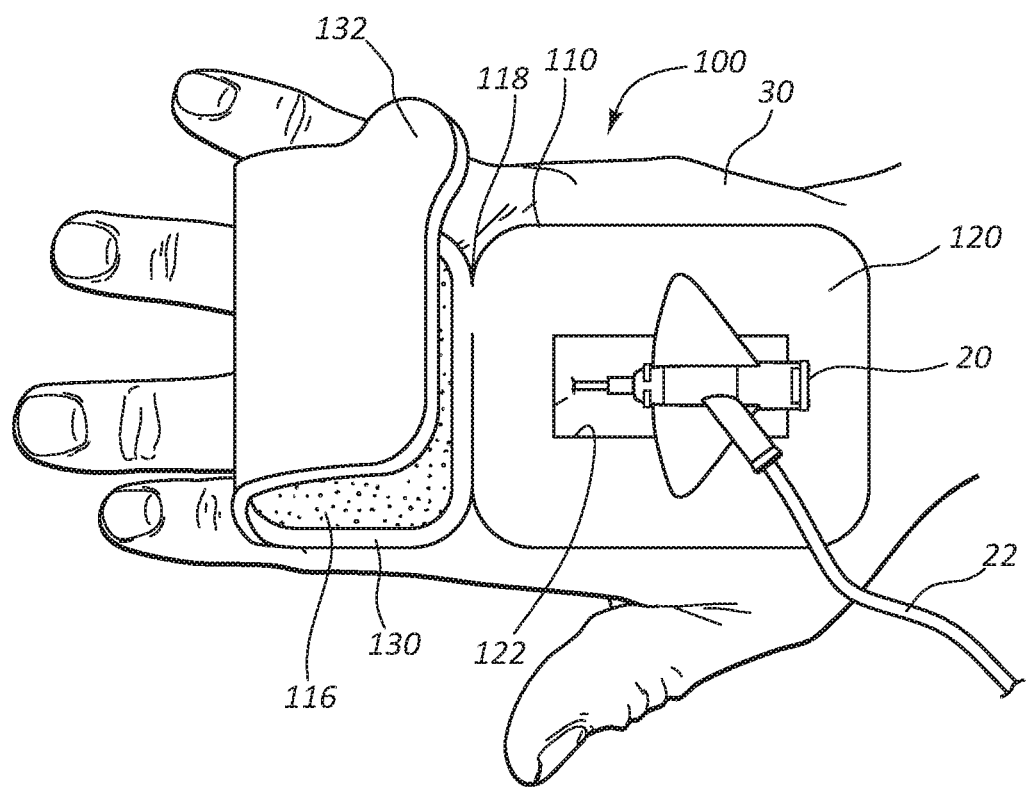
Figure 9:
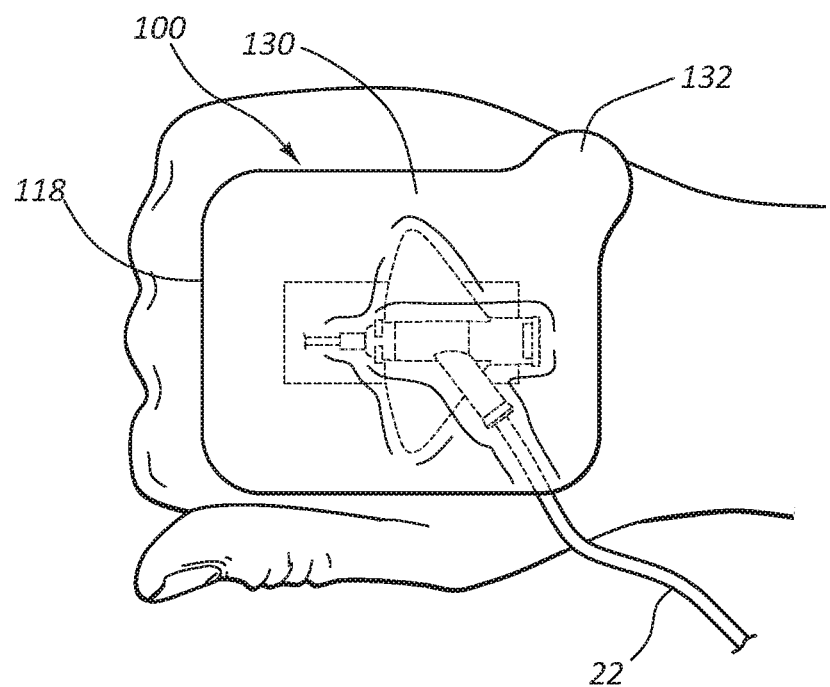
Figure 10:
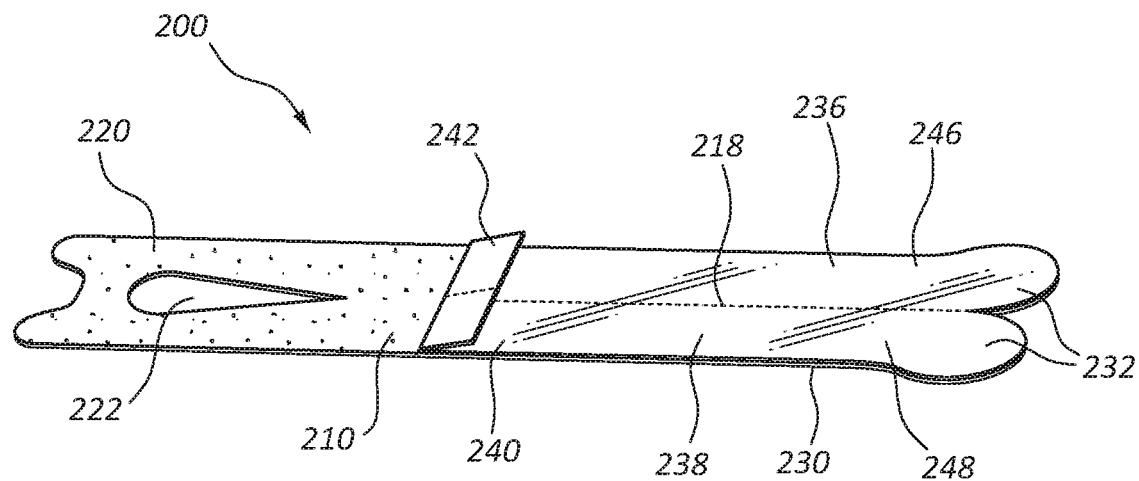
FIG. 10 illustrates a perspective view of an exemplary catheter securement.

As shown in FIGS. 8 and 9, close tab 132 may be free of adhesive layer 116, allowing the clinician to grasp close tab 132 and pull upper portion 130 such that it folds over onto lower portion 120 about fold line 118. Adhesive layer 116 may contact the surface of lower portion 120 and portions of catheter device 20 and tube 22, thereby adhering upper portion 130 to lower portion 120 in a folded configuration and securing catheter device 20 between the upper portion 130 and the lower portion 120 and in position against the skin of patient 30.

FIGS. 10-13 illustrate other embodiments of catheter securements 200. Catheter securement 200 may include a body 210, with a lower portion 220 and an upper portion 230. Upper portion 230 may include separation line 218 to divide upper portion 230 into a first adhesive strip 236 and second adhesive strip 238, as will be further described in more detail below. Lower portion 220 may include adhesive layer on a contact side of lower portion 220 for contact and adhesion with the skin of a patient. Upper portion 230 may include adhesive layer 216 on the opposite side of body 210 from the adhesive layer on lower portion 220 to provide adhesion for the adhesive strips 236, 238 once in place. Release liner 240 may be provided to protect adhesive layer 216 from inadvertent and premature contact until the catheter site is ready for catheter securement 200 to be folded into its final position, as is described in further detail below.

Lower portion 220 may also include opening 222 to provide a window for placement of a catheter so the adhesive strips 236, 238 of upper portion 230 may easily accommodate catheter device 20. In some embodiments, access opening 222 may be a window, enclosed on each lateral side, or it may be a slit or strip opening in lower portion 220 to provide access to the catheter placement site. Similarly, access opening 222 may be any suitable or desirable shape, such as a rectangle, or a square, triangle, or other polygonal shape, or it may be an oval, cartioid, lenticular, or other curved shape suitable for attachment of an intravenous catheter site when catheter securement 200 is affixed to a patient.

Upper portion 230 may include close tabs 232 to provide a gripping area to fold adhesive strips 236, 238 of upper portion 230 to secure catheter device 20. Close tabs 232 may be formed so as to make folding catheter securement 200 intuitive for clinicians using the device. Release liner 240 may also be included on upper portion 230 to protect adhesive layer 216 from inadvertent and premature contact. Release liner 240 may further include release tab 242 to aid in removing release liner 240 when a clinician is ready to fold catheter securement 200 into place. In some embodiments, a second release liner may be provided to protect an adhesive layer on lower portion 220 prior to use. As such, release liners may be placed over any adhesive portion to preserve the adhesive properties and sterility prior to securement to the patient. In some embodiments, release liner 240 may be removed before separating upper portion 230 into adhesive strips 236 and 238, or separate portions 246, 248 of release liner 240 may be removed individually after separating adhesive strips 236, 238.

Figure 11:
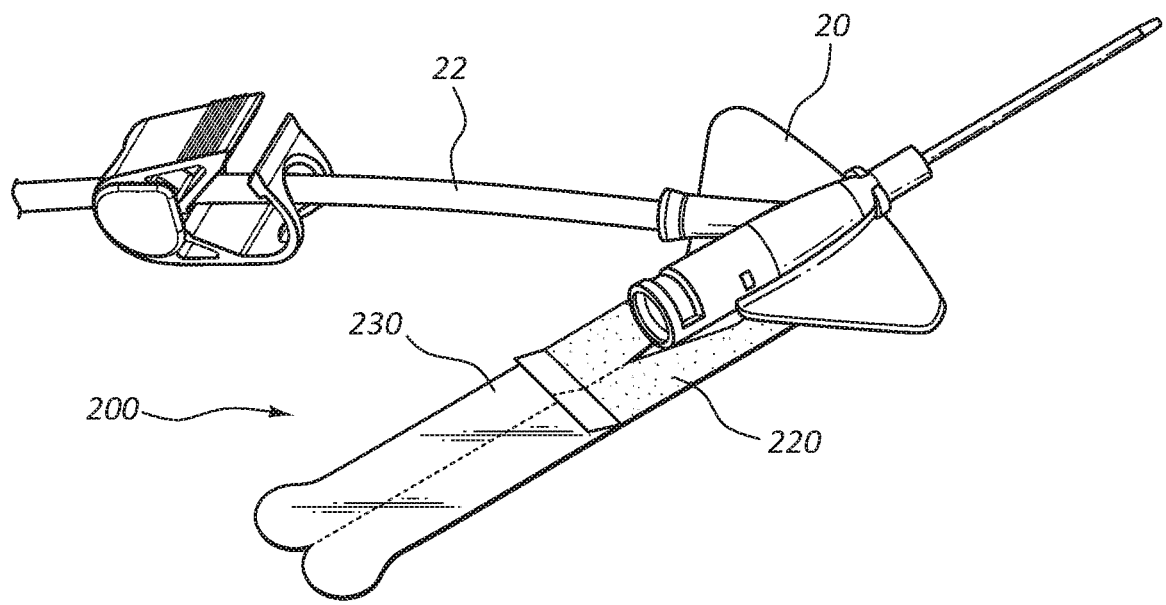
FIGS. 11-13 illustrate a perspective view of an exemplary catheter securement in successive stages of application.
Figure 12:
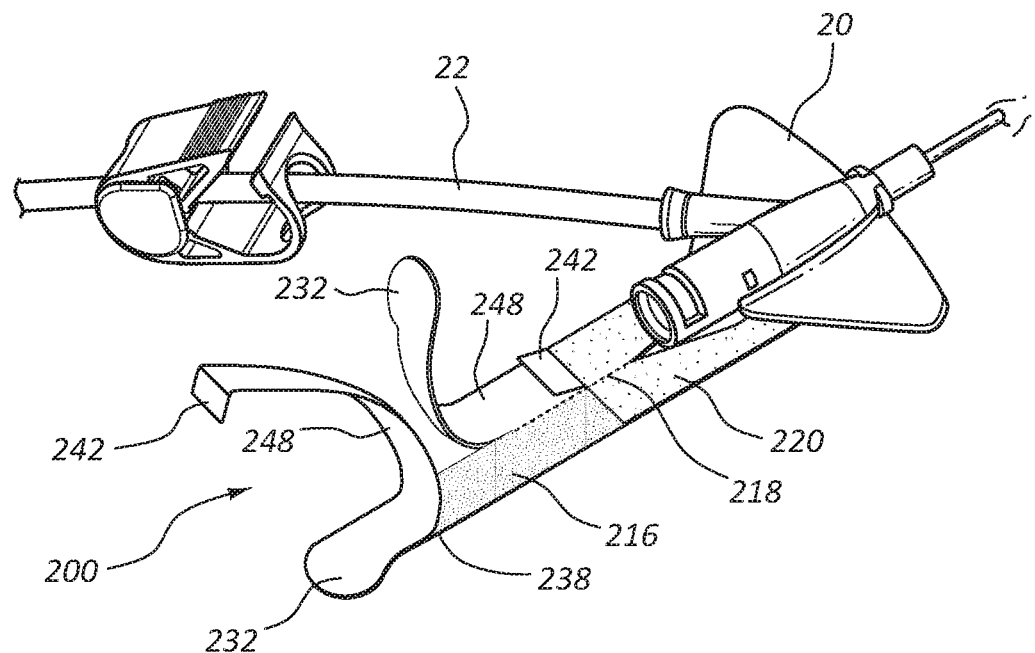
Figure 13:
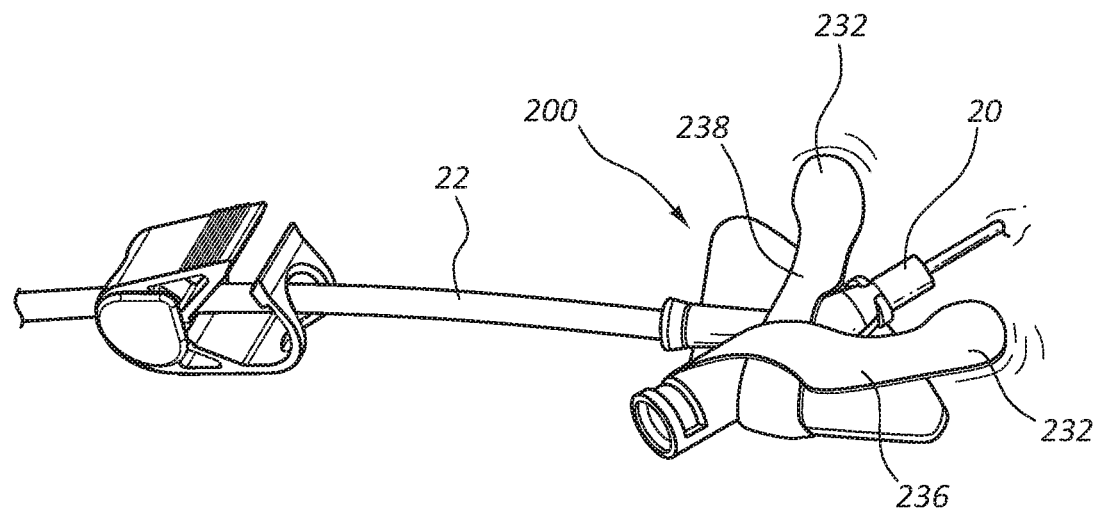

As shown in FIGS. 11-13, catheter securement 200 may be applied to the skin on a patient in preparation for insertion of catheter device 20. In some embodiments, applying catheter securement 200 may include cleaning and preparing the catheter site by a clinician. Once the site on patient is prepared, catheter securement 200 may be removed from a sealed package. Once removed from a sealed package, catheter securement 200 may be positioned over the catheter site on the patient such that the catheter site is accessible so that catheter device 20 may be secured by securement 200. Lower portion 220 may then be pressed onto the skin of the patient so that an adhesive layer attaches lower portion 220 to the skin of the patient. In embodiments where a separate release liner is included with the adhesive layer on lower portion 200, the release liner may be removed prior to placement at the desired catheter site.

Once catheter securement 200 is in position, a clinician may insert catheter device 20 into a patient. Tube 22 may be extended away from catheter device 20 once catheter securement 200 is in final placement and covering catheter device 20. As shown in FIG. 12, once catheter device 20 is placed, release liner 240, or portions 246, 248 of release liner 240, may be removed to expose adhesive layer 216. Release liner 240 may be removed by pulling on release tab 242. Release liner 240 may be disposed of.

Close tabs 232 may be free of adhesive layer 216, allowing the clinician to grasp close tab 232 and pull adhesive strips 236, 238 of upper portion 230 such that the adhesive strips fold over portions of catheter device 20 securing catheter device 20 between the upper portion 230 and the lower portion 220 and in position against the skin of the patient. Adhesive strips 236, 238 may be crossed over catheter device 20, as shown in FIG. 13, or may be secured over any portion of catheter device 20, as desired by a clinician applying securement 200 and catheter device 20.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments, in all respects, are meant to be illustrative only and should not be construed to be limiting in any manner.

The invention claimed is:

1. A catheter securement device, comprising:
   a foldable body, wherein the body includes a distal portion and a proximal portion when the body is in an unfolded position, wherein a lower surface of the distal portion includes a first adhesive layer, wherein the distal portion comprises an access opening entirely enclosed in the distal portion and the first adhesive layer, wherein the proximal portion includes a separation line to divide the proximal portion into a first strip and a second strip, wherein an upper surface of the first and second strip includes a second adhesive layer.

2. The catheter securement device of claim 1, further comprising a release liner removably coupled to the second adhesive layer.

3. The catheter securement device of claim 1, wherein the distal portion further comprises an access opening.

4. The catheter securement device of claim 3, wherein the access opening includes an enclosed window.

5. The catheter securement device of claim 3, wherein the access opening includes a slit.

6. The catheter securement device of claim 1, wherein the proximal portion further comprises a tab.

7. The catheter securement device of claim 6, wherein the tab is disposed at a proximal end of the first strip when the body is in the unfolded position.

8. The catheter securement device of claim 6, wherein the tab is a first tab, wherein the proximal portion further comprises a second tab, wherein the first tab is disposed at a proximal end of the first strip when the body is in the unfolded position, wherein the second tab is disposed at a proximal end of the second strip when the body is in the unfolded position.

9. The catheter securement device of claim 8, wherein the first and second tabs do not include the second adhesive layer.

10. The catheter securement device of claim 8, further comprising a release liner removably coupled to the second adhesive layer, wherein the release liner covers the first and second tabs.

* * * * *